United States Patent [19]

Logothetis et al.

[11] Patent Number: 4,841,934

[45] Date of Patent: Jun. 27, 1989

[54] OXYGEN PUMPING DEVICE FOR CONTROL OF THE AIR FUEL RATIO

[75] Inventors: Eleftherios M. Logothetis, Birmingham; Robert E. Hetrick, Dearborn Heights; Richard E. Soltis, Redford; William C. Vassell, Birmingham, all of Mich.

[73] Assignee: Ford Motor Company, Dearborn, Mich.

[21] Appl. No.: 17,292

[22] Filed: Feb. 20, 1987

[51] Int. Cl.⁴ .............................................. F02D 41/14
[52] U.S. Cl. .................................. 123/440; 204/1 T; 204/406
[58] Field of Search ............... 123/440, 489, 589; 60/276; 204/406, 1 T, 407, 424

[56] References Cited

U.S. PATENT DOCUMENTS

| | | | |
|---|---|---|---|
| 4,169,440 | 10/1979 | Taplin et al. | 123/489 |
| 4,272,329 | 6/1981 | Hetrick et al. | 204/1 T |
| 4,272,330 | 6/1981 | Hetrick | 204/1 T |
| 4,272,331 | 6/1981 | Hetrick | 204/1 T |
| 4,499,880 | 2/1985 | Miki et al. | 123/489 |
| 4,615,787 | 10/1986 | Yamada et al. | 123/440 |

OTHER PUBLICATIONS

"Honda LEAN-BURN Concept", Apr. 25, 1986 at Luxemburg International Conference.

*Primary Examiner*—Andrew M. Dolinar
*Attorney, Agent, or Firm*—Peter Abolins; Clifford L. Sadler

[57] ABSTRACT

A method of controlling the air fuel ratio of an internal combustion engine includes positioning a two cell oxygen pumping device in the exhaust gas of the engine. A pumping current is applied to a pumping cell and an EMF is sensed across a sensor cell. The sensed EMF is compared to reference voltage and an error signal is generated. The air fuel ratio is changed in response to the error signal so as to reduce the absolute magnitude of the error signal.

1 Claim, 2 Drawing Sheets

OXYGEN PUMPING DEVICE FOR CONTROL OF THE AIR FUEL RATIO

BACKGROUND OF THE INVENTION

1. Technical Field

This invention relates to controlling the air-to-fuel ratio of a combustion process, in particular the combustion process in an internal combustion engine.

2. Prior Art

In recent years, high temperature solid state oxygen sensors have been used extensively for control of the air-to-fuel ratio, A/F, of internal combustion engines. The most widely used device is a simple Nernst concentration $ZrO_2$ cell which gives an output EMF proportional to the natural logarithm of the oxygen partial pressure of the exhaust gas ($P_O$, exh), $$EMF = \frac{RT}{4F} \ln(P_{0,exh}/P_{0,ref}),$$

where $P_{O,ref}$ is the oxygen partial pressure of a reference atmosphere, e.g. air, F and R are the Faraday and the ideal gas constants, and T is the absolute temperature. Despite the sensor's low sensitivity to oxygen partial pressure, the large change in oxygen pressure at the stoichiometric A/F ratio allows the successful use of these sensors for stoichiometric A/F engine control. On the other hand, the usefulness of these sensors in the lean A/F region of the weak dependence of $P_{O,exh}$ on A/F in the lean region. Recently, a number of oxygen sensors with lean A/F measurement capabilities have been reported. These devices are commonly called lean exhaust gas oxygen, LEGO, sensors. The devices are based on oxygen pumping with $ZrO_2$ cells and provide an output which generally is linearly proportional to the oxygen partial pressure. Their high sensitivity to oxygen pressure combined with low temperature sensitivity make these sensors promising for lean A/F engine control.

A double $ZrO_2$ cell sensor described by Hetrick et al (U.S. Pat. Nos. 4,272,331, 4,272,330 and 4,272,329) includes two $ZrO_2$ electrochemical cells, one used as an oxygen pumping cell and the other as an oxygen sensing cell. FIG. 1 shows schematically the structure of this sensor. The device is immersed in the exhaust gas and a current $I_p$ is passed through pumping cell 10 that pumps oxygen out of the cavity 11. This pumping action lowers the oxygen pressure inside cavity 11 and induces a diffusional flux of oxygen from the exhaust into the cavity 11 through the aperture 12 and, at the same time, causes an EMF $V_s$ to develop across a sensor cell 13. At steady state, the flux of oxygen pumped out of cavity 11 by the current is equal to the diffusional flux of oxygen into cavity 11 and the following relation between $I_p$, $V_s$ and $P_{O,exh}$ is then valid:

$$I_p = 4e\sigma P_{0,exh}(1-\exp(-4FV_s/RT)) \quad (1)$$

where e is the electron charge, F and R are the Faraday and the ideal gas constants, T is the absolute temperature and $\sigma$ is a constant that depends on the geometrical characteristics of the aperture 12 and the diffusion constant of oxygen.

During operation of the device, the current $I_p$ is adjusted so that the voltage $V_s$ is kept constant (e.g. 50 mV). This is accomplished with a feedback circuit which compares the EMF, $V_s$, with a reference voltage $V_r$. Under these conditions, $I_p$ is proportional to $P_{O,exh}$.

FIG. 2 shows the dependence of the current output $I_p$ of this device on the air-to-fuel ratio of an engine. To control the A/F ratio at a desired $(A/F)_c$, an external feedback circuit is used which compares the sensor output $V = I_pR$ with a reference voltage $V_c = (I_p)_cR$ corresponding to the desired $(A/F)_c$ (see FIG. 1b). This comparison could be done in an on-board computer utilizing what is commonly called a "look-up table", a tabulation of $V_c$ vs A/F which is essentially a calibration curve for the device. If V is different than $V_c$, the external feedback circuit adjusts the A/F ratio (e.g. by adjusting the amount of fuel) until V becomes equal to $V_c$.

A number of single $ZrO_2$ cell $O_2$ pumping devices have also been described, in which the single $ZrO_2$ cell acts as both an $O_2$ pump and an $O_2$ sensor. The "diffusion barrier" in these devices is formed either by a porous inactive layer (e.g. spinel) or by a small cavity with an aperture. If one applies a sufficiently high voltage across the $ZrO_2$ cell, the pumping current attains a limiting value (saturation current) which is proportional to the partial pressure of $O_2$ in the ambient (exhaust gas). Saturation represents the complete depletion of $O_2$ at the negative electrode.

In addition to $O_2$ pumping-based sensors intended for lean operation, devices have also been described which can operate over an extended A/F range from very lean to very rich A/F mixtures. These devices are commonly called universal exhaust gas oxygen, UEGO, sensors. One example of this type of sensors was discussed by Vassell et al in Society of Automotive Engineers Paper #841250.

Double-cell oxygen-pumping devices such as the one described by Hetrick et al have several advantages over the single-cell sensors. These include insensitivity to electrode properties, operation not limited by the resistance of the $ZrO_2$ material and more effective optimization with respect to response time and temperature sensitivity. Double-cell sensors, on the other hand, are more complex in structure, electronics and operation. It would be desirable, therefore, to develop devices which preserve the essential advantages of the above-mentioned double-cell sensors but are simpler. These are some of the advantages of the present invention.

SUMMARY OF THE INVENTION

In accordance with an embodiment of this invention, a method of operating a two cell oxygen pumping device includes applying a pumping current to a pumping cell and comparing a measured EMF, $V_s$, across a sensor cell with a reference voltage $V_R$. Such a device can be used to control the air fuel ratio of an engine. The error signal output from the comparison is used to control adjustment of the air fuel ratio by changing, for example, the amount of fuel.

If the air fuel ratio of the engine is leaner (i.e., larger) than the desired value, the current is not sufficiently large and $V_s$ becomes smaller than the reference voltage $V_R$. A positive error signal directs the fuel metering device to decrease the engine air fuel ratio until $V_s$ becomes equal to the reference voltage. If, on the other hand, the air fuel ratio is richer (i.e., smaller) than the desired value, the current is too large and the measured $V_s$ becomes larger than the reference voltage. A negative error signal, $V_R$ minus the measured $V_s$, directs then the fuel metering device to increase the engine air fuel ratio until the measured $V_s$ becomes equal to the reference voltage. In accordance with one embodiment of this invention, to control the air fuel ratio of the engine at another value, the pumping current must be changed to a new value corresponding to the air fuel ratio value. The value of the reference voltage is maintained the same.

Operation of a two cell pumping device in accordance with this invention produces a high sensitvity air fuel ratio sensor for control of air fuel ratio of an engine away from stoichiometry. Operation in accordance with this method eliminates the need for an internal feedback circuit such as used in the prior art. This results in a simpler, less expensive, and a faster device, by eliminating the extra response time arising from the feedback circuit.

DISCLOSURE OF THE INVENTION

Figure 1:
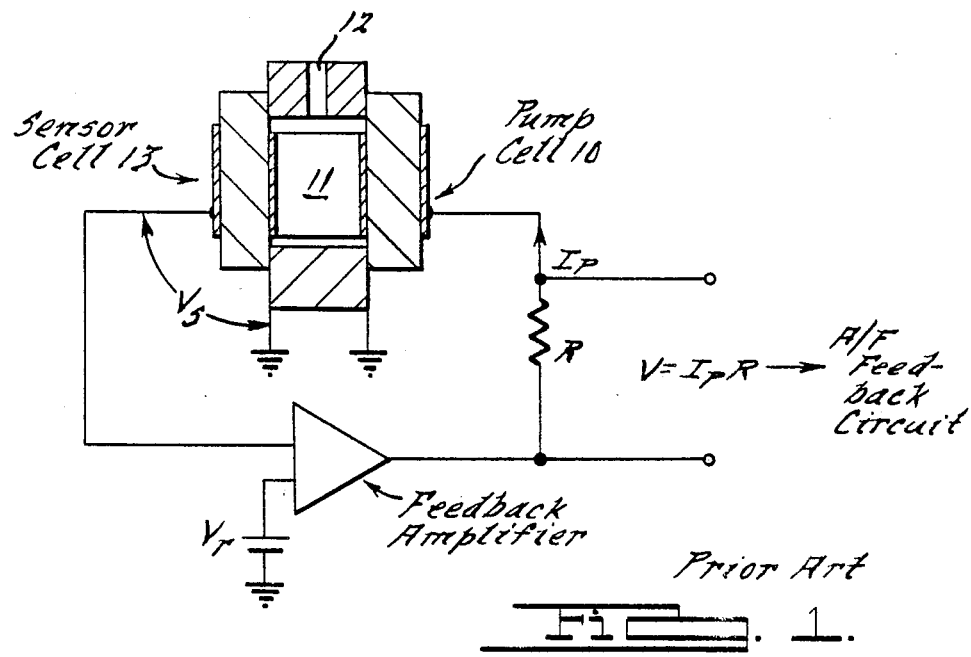
FIG. 1 is a schematic, partly cross-section diagram of an oxygen pumping device using two cells and a feedback circuit in accordance with the prior art.
Figure 4:
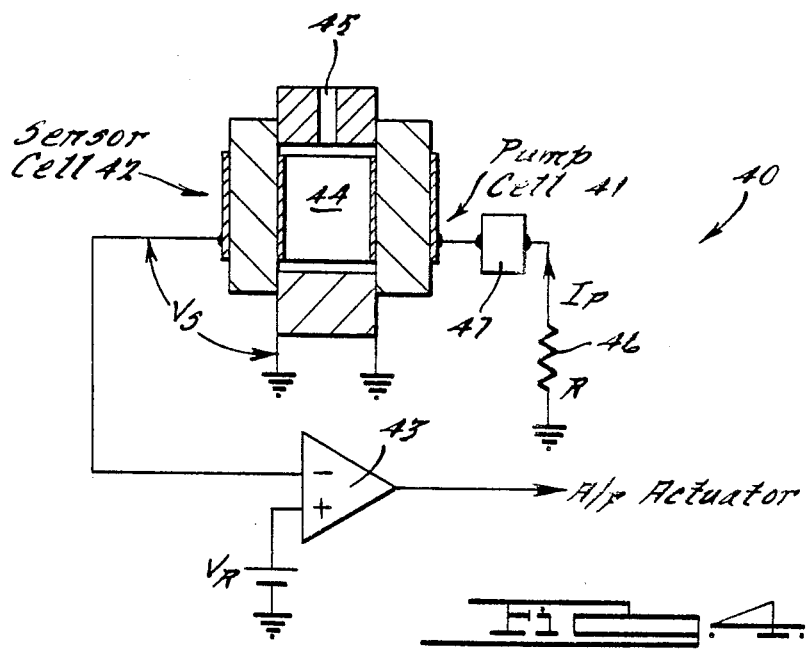
FIG. 4 is a schematic, of a two cell pump device and circuit in accordance with an embodiment of this invention.

The description of the structure and principle of operation described in U.S. Pat. No. 4,272,329 to R. E. Hetrick and W. A. Fate are incorporated herein by reference. Referring to FIG. 4, a device 40 is used to control the A/F ratio of an engine without the use of the internal feedback circuit shown in FIG. 1. Device 40 includes a pump cell 41 and a sensor cell 42 adjacent a cavity 44 which is in communication with the ambient exhaust gas through an aperture 45. Pump cell current, $I_p$, is applied to pump cell 41 through a resistor 46 by means of a power supply 47. The sensed voltage, $V_S$, across sensor cell 42 is applied to the negative input of a comparator 43. A reference voltage $V_r$, is applied to the positive input of comparator 43. The output of comparator 43 is applied to an air fuel actuator so as to adjust the air fuel ratio of the internal combustion engine generating the exhaust gas being sensed.

Equation 1 can be rearranged to give the following expression for $V_s$ $$-V_s = RT/4F \ln(1 - I_p/(4e\sigma P_{O,exh})). \tag{2}$$

In a first method of operation, the value of the pumping current $I_p$ is kept constant, in which case the EMF of the sensing cell, $V_s$, becomes a unique function of $P_{O,exh}$ according to equation 2.

Figure 3:
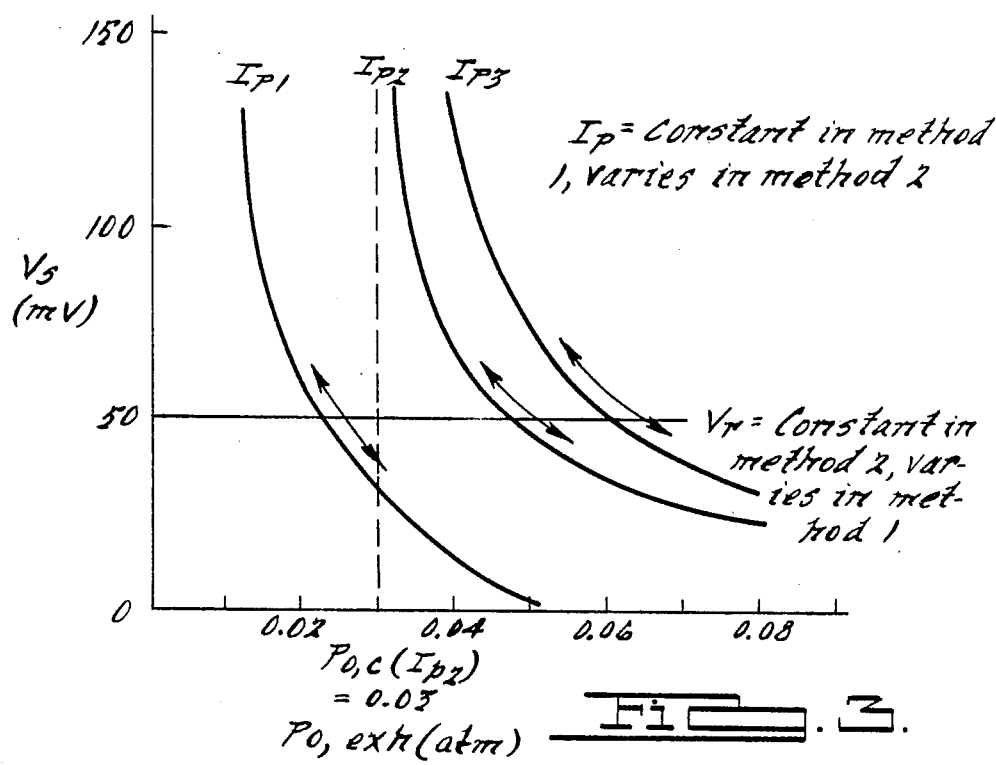
FIG. 3 is a graph relating partial oxygen pressure in the exhaust gas and sensor voltage of a circuit in accordance with an embodiment of this invention.

FIG. 3 shows the expected behavior of device 40 operated in this mode. For large values of P, $V_s$ varies as $1/P_{O,exh}$. This can be seen by expanding the natural logarithm in equation 2 for $I_p/(4e\sigma P_{O,exh}) << 1$. For small values of $P_{O,exh}$, $V_s$ increases more rapidly with decreasing $P_{O,exh}$ and attains very large values as $P_{O,exh}$ approaches in magnitude a critical value $P_{O,C}$ (0.03 atm in FIG. 3 for the $P_{O,C}$ associated with $I_{p2}$) that satisfies the condition $4e\sigma P_{O,C} = I_p$. This condition corresponds to the case wherein $P_{O,C}$ is sufficiently low so that the pumping current can completely remove all oxygen from inside the cavity.

It is apparent from FIG. 3 that the device has higher sensitivity for $P_{O,exh}$ values close to $P_{O,C}$. If one wants to measure or control the oxygen pressure at higher $P_{O,exh}$ values with higher sensitivity, the pumping current should be increased so that the curve in FIG. 3 is shifted to the right (e.g., $I_{p3}$). On the other hand, if one wants to operate at $P_{O,exh}$ values less than $P_{O,C}$, the pumping current should be decreased so that the curve is shifted to the left (e.g., $I_{p1}$). The smaller the pumping current is, the larger is the A/F range that can be measured and/or controlled without a change in the current. On the other hand, the sensitvity of the device becomes smaller for the higher values of $P_{O,exh}$.

The control of the A/F ratio of an engine with this device can be accomplished by employing either of two different methods. In the first method, an appropriate pumping current $I_p$ (a constant current selected from among, e.g., $I_{p1}$, $I_{p2}$, $I_{p3}$) is sent through pumping cell 41 and the EMF, $V_s$, of sensing cell 42 is compared with a reference voltage $V_r$ (FIG. 4) in comparator 43. The voltage, $V_r$, varies and is chosen from a $V_s$ vs A/F calibration curve (similar to that of FIG. 3) to have the value $(V_s)_c$ which corresponds to the desired value $(A/F)_c$. The error signal from the comparator is used to change directly the A/F ratio by changing, for example, the amount of fuel. If the A/F ratio of the engine is leaner than the desired value $(A/F)_c$, the current $(I_p)_c$ is not sufficiently large and $V_s$ becomes smaller than $(V_s)_c$. A positive error signal, $(V_s)_c - V_s$, directs the fuel metering device to decrease the engine A/F ratio until $V_s$ becomes equal to $(V_s)_c$.

If, on the other hand, the A/F ratio is smaller than the desired value $(A/F)_c$, the current $(I_p)_c$ is too large and $V_s$ becomes larger than $(V_s)_c$. A negative error signal, $(V_s)_c - V_s$, directs then the fuel metering device to increase the engine A/F ratio until $V_s$ becomes equal to $(V_s)_c$. To control the A/F ratio of the engine at another value $(A/F)_c'$, the reference voltage must be changed to a new value $(V_s)_c'$ corresponding to the desired value $(A/F)_c'$. The choice of the value of the pumping current $I_p$ is a compromise between high device sensitivity and wide A/F range of control as discussed in the previous paragraph and in the next section.

Figure 2:
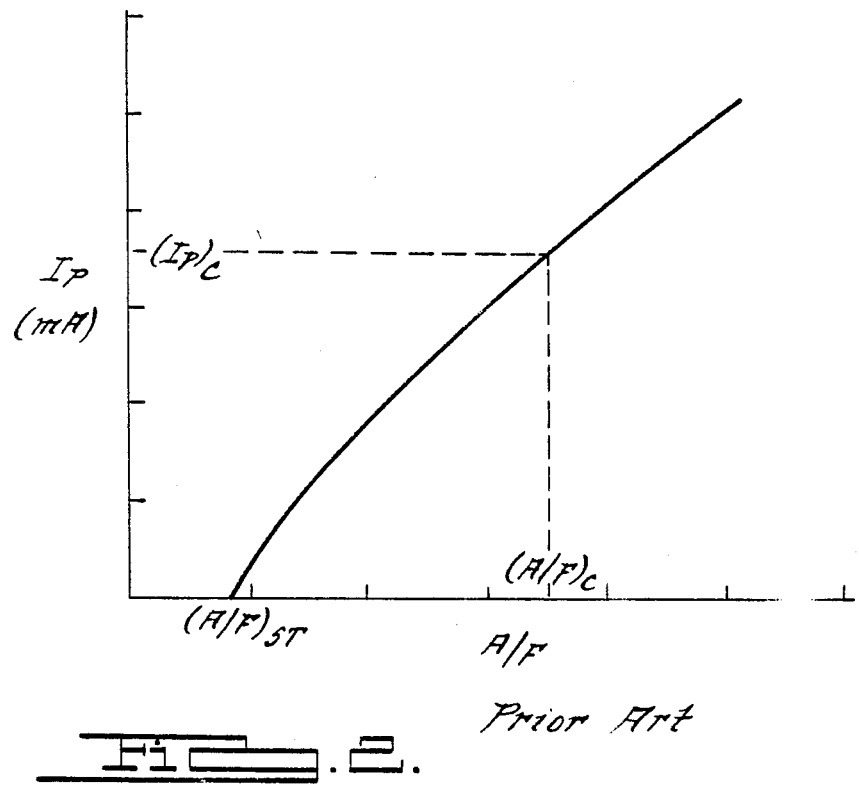
FIG. 2 is a graph relating air fuel ratio and the pump current of the prior art circuit shown in FIG. 1.

In the second method of controlling the A/F ratio of an engine with the present device, the reference voltage $V_r$ is set at a constant value (e.g. 50 mV). To control the A/F ratio at a desired value $(A/F)_c$, a pumping current is sent through the pumping cell having a magnitude $(I_p)_c$ such that the EMF, $V_s$, across the sensing cell is equal to $V_r$ (FIG. 2b). That is, for different magnitude $I_p$ curves, $V_s$ varies along these different curves. If the A/F ratio is leaner than $(A/F)_c$, the current $(I_p)_c$ is not sufficiently large and $V_s$ becomes smaller than $V_r$. If the A/F ratio is richer than $(A/F)_c$, the current $(I_p)_c$ is too large and $V_s$ becomes larger than $V_r$. The error signal, $V_r - V_s$, directs the fuel metering system to increase or decrease the A/F ratio until $V_s$ becomes equal to $V_r$. To control the A/F ratio at another value $(A/F)_c'$, the pumping current must be changed to a new value $(I_p)_c'$ by adjusting the magnitude of power supply 47.

If the A/F ratio is controlled only at one constant value, then there is no difference in operation for methods one and two. However, when one decides to operate at a different A/F ratio, one changes $V_r$ in method one and changes $I_p$ in method two. Changing $I_p$, in method two, offers higher sensitivity over a wider A/F range. Thus, in method two, by changing $I_p$ and holding $V_r$ fixed, one can stay on or near a rapidly rising portion of the curve in FIG. 3 for each chosen A/F ratio. However, in accordance with method one, with $I_p$ fixed, as $V_r$ is changed to a low value for leaner A/F ratio control, it takes large changes in A/F ratio to get a small change in $V_s$ and one has low sensitivity.

In summary, the sensitivity and accuracy of the disclosed sensing system as an A/F ratio control device depends on whether method one or method two is employed. With method one, if control of the A/F ratio at more than one value is desired, the fixed value of the pumping current must be selected sufficiently small so that the entire A/F range of control falls within the sensor characteristic (see FIG. 3). In this case, the sensitivity (and accuracy) of the device decreases with increasing A/F and, for the most part of the A/F range, is lower than that of the original LEGO sensor. When method two is employed, each time the A/F value of control is changed, the pumping current $I_p$ is also changed to a value which, by shifting the curve of FIG. 3, brings the control A/F value on the steep portion of the curve. In this case, the sensitivity (and accuracy) of the device remains high for all A/F values and is approximately the same as that of our original sensor. For this reason, method two is preferable to method one. If it is desirable to control the A/F ratio only at one value, then methods one and two are equivalent.

These methods of operation are applicable not only to a LEGO but also to an UEGO sensor. To operate in the rich A/F region, only the direction of the pumping current needs to be changed, the rest of the operation remaining the same.

Various modifications and variations will no doubt occur to those skilled in the art to which this invention pertains. For example, the particular construction of the two cell oxygen pumping device may be varied from that disclosed herein. These and all other variations which basically rely on the teachings through which this disclosure has advanced the art are properly considered within the scope of this invention.

We claim:

1. A method operating a two cell oxygen pumping device to control the air fuel ratio of an engine, the oxygen pumping device having a pumping cell and sensing cell, includes the steps of:
    introducing exhaust gas from the engine to a region between the pumping cell and the sensing cell;
    applying a pumping current to the pumping cell;
    sensing an EMF across the sensing cell;
    comparing an adjustable reference voltage with the sensed EMF;
    generating an error signal from the comparison between the reference voltage and the sensed EMF;
    changing the air fuel ratio in response to the error signal so as to reduce the absolute magnitude of the error signal, including the step of decreasing the engine air fuel ratio in response to a positive error signal until the measured EMF becomes equal to the reference voltage, and the step of increasing the engine air fuel ratio in response to a negative error signal until the measured EMF becomes equal to the reference voltage;
    establishing a predetermined desired air fuel ratio from a range of possible operating air fuel ratio values;
    establishing a predetermined desired pumping current which remains fixed for any given air fuel ratio value within said range; and
    adjusting the reference voltage to a new value, consistent with the fixed desired pumping current, when it is desired to change the actual air fuel ratio, so as to cause the actual air fuel ratio magnitude to change until it is equal to the predetermined desired air fuel ratio.

* * * * *